(12) United States Patent
Buck et al.

(10) Patent No.: US 8,728,164 B2
(45) Date of Patent: May 20, 2014

(54) IMPLANT FOR SURGICAL USE IN HUMANS OR VERTEBRATES

(75) Inventors: Alfred Ernst Buck, Bondorf (DE);
Hans-Peter Kaps, Tuebingen (DE)

(73) Assignee: Buck GmbH & Co. KG, Bondorf (DE)

( * ) Notice: Subject to any disclaimer, the term of this patent is extended or adjusted under 35 U.S.C. 154(b) by 2213 days.

(21) Appl. No.: 11/211,049

(22) Filed: Aug. 24, 2005

(65) Prior Publication Data

US 2006/0052873 A1   Mar. 9, 2006

(30) Foreign Application Priority Data

Aug. 25, 2004   (DE) .......................... 10 2004 041 354

(51) Int. Cl.
*A61F 2/44*   (2006.01)

(52) U.S. Cl.
USPC .................. 623/17.16; 623/17.13; 623/23.54

(58) Field of Classification Search
USPC ................................ 623/17.11–17.16, 23.54
See application file for complete search history.

(56) References Cited

U.S. PATENT DOCUMENTS

| | | | | |
|---|---|---|---|---|
| 5,030,233 | A * | 7/1991 | Ducheyne ................... | 623/23.54 |
| 5,329,846 | A * | 7/1994 | Bonutti ........................... | 100/50 |
| 5,492,768 | A * | 2/1996 | Okimatsu et al. ............. | 428/549 |
| 5,534,030 | A * | 7/1996 | Navarro et al. ............. | 623/17.15 |
| 6,093,205 | A * | 7/2000 | McLeod et al. ............. | 623/17.16 |
| 6,461,385 | B1 * | 10/2002 | Gayer et al. ................ | 623/23.51 |
| 6,752,831 | B2 * | 6/2004 | Sybert et al. ................ | 623/13.17 |
| 6,827,743 | B2 * | 12/2004 | Eisermann et al. ........ | 623/23.54 |
| 7,066,960 | B1 * | 6/2006 | Dickman .................... | 623/17.16 |
| 7,153,325 | B2 * | 12/2006 | Kim et al. ................... | 623/17.15 |
| 7,238,205 | B2 * | 7/2007 | Karahalios ................. | 623/17.11 |
| 7,291,172 | B2 * | 11/2007 | Marissen .................... | 623/17.12 |
| 7,503,933 | B2 * | 3/2009 | Michelson ................. | 623/17.11 |
| 7,905,921 | B2 * | 3/2011 | Kim et al. ................... | 623/17.16 |
| 8,475,503 | B2 * | 7/2013 | Denoziere et al. ............ | 606/279 |
| 8,545,565 | B2 * | 10/2013 | Van Den Broek et al. . | 623/17.16 |
| 2002/0098245 | A1 * | 7/2002 | Constantz ..................... | 424/602 |
| 2002/0107569 | A1 * | 8/2002 | Katsura ....................... | 623/11.11 |
| 2005/0015154 | A1 * | 1/2005 | Lindsey et al. ............. | 623/23.46 |
| 2005/0027364 | A1 * | 2/2005 | Kim et al. ................... | 623/17.13 |
| 2006/0041262 | A1 * | 2/2006 | Calvert et al. ................. | 606/76 |

FOREIGN PATENT DOCUMENTS

| | | | |
|---|---|---|---|
| DE | 9219092.1 | 11/1992 | |
| DE | 4417629 | 1/1995 | ............... A61F 2/44 |
| DE | 69020254 T | 1/1996 | ............... C07K 4/00 |
| DE | 69126971 T | 2/1998 | ............... A61F 2/44 |

(Continued)

OTHER PUBLICATIONS

Office Action dated Mar. 23, 2009 corresponding to German Patent Application No. 10 2004 041 354.1.

(Continued)

*Primary Examiner* — Michael T Schaper
(74) *Attorney, Agent, or Firm* — Ohlandt, Greeley, Ruggiero & Perle, LLP (57) ABSTRACT

A process for the production of an implant and to an implant for surgical use in humans or vertebrates, in particular for the replacement, for the partial replacement or for the strengthening of a damaged intervertebral disk or for the replacement, for the partial replacement or for the strengthening of an anatomical joint. The implant includes at least one wire or at least one fiber. The wire or the fiber is present at least partially as a knitted fabric.

17 Claims, 5 Drawing Sheets

(56) References Cited

FOREIGN PATENT DOCUMENTS

| | | | | |
|---|---|---|---|---|
| DE | 69428143 | T | 5/2002 | ................ A61F 2/44 |
| DE | 1011863 | | 10/2002 | ............. A61L 27/04 |
| DE | 69623535 | T | 2/2003 | ................ A61F 2/44 |
| DE | 60000877 | T | 8/2003 | ............. A61L 27/36 |
| DE | 20315960 | U | 2/2004 | ................ A61F 2/28 |
| DE | 69723905 | T | 7/2004 | ............. A61L 31/02 |
| DE | 69532528 | T | 1/2005 | ................ A61F 2/44 |
| DE | 600009956 | T | 4/2005 | ............... C12N 5/00 |
| EP | 0225838 | | 1/1986 | |
| EP | 0366018 | | 10/1989 | |
| EP | 0505634 | | 9/1992 | |
| EP | 0631763 | | 1/1993 | |
| EP | 0591976 | | 7/1993 | |
| WO | WO2005/011523 | | 2/2005 | |

OTHER PUBLICATIONS

Search report dated Apr. 24, 2009 for parallel European Application No. 09003004.0.

\* cited by examiner

IMPLANT FOR SURGICAL USE IN HUMANS OR VERTEBRATES

CROSS-REFERENCE TO RELATED APPLICATIONS

This application claims the benefit under 35 U.S.C. §119 (a) of German Application No. 10 2004 041354.1-35, filed Aug. 25, 2004, the entire contents of which are incorporated by reference herein.

BACKGROUND OF THE INVENTION

1. Field of the Invention

The invention relates to an implant for surgical use in humans or vertebrates, in particular for the replacement, for the partial replacement or for the strengthening of a damaged intervertebral disk or for the replacement, for the partial replacement or for the strengthening of an anatomical joint.

2. Description of Related Art

The supporting structure of the human body, the skeleton, is composed of bone and cartilage. Together with tendons, ligaments and muscles, it forms the musculoskeletal system in humans and vertebrates.

Here, the joints serve as connection sites between the bones and are responsible for the mobility of the body. In addition to guaranteeing mobility, the joints here especially additionally perform the absorption or compensation of the pressure on the skeletal system which results on standing and jumping. The inter-vertebral disk which lies between each two adjacent vertebrae in man and vertebrates also has this task.

For example, in humans alone the vertebral joints and the joints in the hip and knee are stressed just by standing upright and walking. As a result of wear processes, caused, inter alia, by age, disease or overstressing, wear of the joints or vertebrae or the joint surfaces results. Under certain circumstances, this leads to restricted mobility, decrease in strength or pain. This can be compensated, however, by a replacement, a partial replacement or a strengthening of the joints by means of an implant.

Here, the implant should essentially correspond to the dimensions and the shape of the joint to be replaced or of the intervertebral disk to be replaced, have adequate biocompatibility with the surrounding tissue and especially comparable physical properties, in particular with respect to rigidity, elasticity, resilience and damping, and make possible unrestricted movement within the course of natural movement and have a long lifetime in order not to stress a patient by frequent implant changes.

To this end, a multiplicity of different implants have been provided. For example, in the case of a joint, such as a shoulder, hip or knee joint, the joint capsule or condyle and socket are exchanged with plastic implants, which must be firmly anchored in the bone. In this connection, a distinction is made between the total endoprosthesis, in which both the condyle and socket are replaced, and the partial endoprosthesis in which only the condyle is replaced.

Further known materials or material combinations for forming the joint coupling, i.e. for forming the socket and condyle or for forming the surfaces of the socket and condyle rubbing on one another, include the coupling of metal/metal, plastic/metal, plastic/ceramic or ceramic/ceramic. In the selection of the material combination, in addition to the biocompatibility, the long-term anchoring of the implant in the body, the wear and the abrasion on the joint surfaces of the artificial joint play a crucial role. Here, the abrasion depends on the materials of the joint coupling. Plastics disadvantageously exhibit increased wear on account of increased abrasion compared with metal surfaces or ceramic surfaces which are precisely ground with respect to one another.

The structures of the bones or of the joints are adjusted in their function, especially with respect to rigidity, elasticity, resilience and damping, such that they optimally conform to the local stress. This functionally adjusted structure is disturbed by the incorporation of an implant on account of changed extension behavior and changed force transmission by the implant, especially in the case of metals or ceramics, in the bones. The force transmission of the implant in the bones in this case plays a crucial role in the question of the long-term anchoring or fixing of the implant in the body.

Moreover, in order to guarantee solid growing together of the implant with the bone by bone ingrowth into the implant, the outsides of the implants oriented toward the bone are provided with a surface structuring.

For the replacement of intervertebral disks, the specification DE 696 23 535 T2, for example, discloses an artificial intervertebral disk which has a two-part, hard, chromium-coated metallic ball joint bearing system and makes possible unrestricted movement, but at the same time is unable to absorb shocks to the spinal column. Moreover, the surfaces of the ball joint bearing system moving on or against one another must be precisely and therefore expensively processed in order to avoid or to minimize accelerated wear of the surfaces caused, inter alia, by friction.

The document DE 694 28 143 T2 discloses, for the replacement of a damaged intervertebral disk, an intervertebral disk prosthesis which comprises an upper rigid plate, a lower rigid plate and an elastomeric core, which is arranged between the plates and adjoins these. Owing to its elastomeric core, this implant exhibits shock absorption and, together with low rigidity, adequate mobility. However, the elastomeric core can be degraded by the body over time. Moreover, elastomers tend to deform over time and thereby to change their dimensions and properties.

Both implants have projections on the outsides oriented in the direction of the vertebrae in order to fix the implant into the vertebrae. Moreover, in both implants said outsides are additionally provided with a porous coating in order to make possible an ingrowth of tissue or bone ingrowth into the implant by the surrounding vertebrae and thereby to connect the bone more strongly with the implant.

BRIEF SUMMARY OF THE INVENTION

Against this background, the present invention is therefore based on the object of avoiding the above-mentioned disadvantages of the prior art, not only for implants for the replacement, for the partial replacement or for the strengthening of intervertebral disks, but also for joints.

This comprises the aim of making available an implant which makes possible unrestricted movement within the course of natural movement (bending, tilting and rotating movements or else alternatively translation movements) and moreover has the property of shock absorption due to its elasticity, its resilience and internal damping.

Moreover, the implant should be biocompatible and at the same time still have a surface which makes possible ingrowth of tissue in order to guarantee a strong connection between the implant and the surrounding tissue and thereby improved stability without it being necessary to attach additional devices to the implant for fixing in the tissue.

Moreover, the implant should be of as stable a shape and as low-wearing as possible and should not be able to be undesirably degraded or changed in its dimensions by the body even over a relatively long period of time and suffer no or at least only low wear damage due to the bone surface.

Furthermore, the implant should be economical to produce in a simple process and to employ by conventional orthopedic surgery known in this field.

In particular, the implant should be able to be adapted, by a simple variation of the production parameters, in particular with respect to its rigidity, elasticity and its resilience and internal damping, to the desired characteristics or specifications of the corresponding joint or intervertebral disk to be replaced or to be supported in order to guarantee the best possible force transmission from the implant to the bone or the surrounding tissue.

Since an implant constructed from a number of constituents can complicate and raise the price of production and surgical incorporation into the body, the implant should have a simplified construction and, under certain circumstances, even advantageously be constructed of only one part.

This object is achieved in a surprising manner by the implant and the process for its production as disclosed herein.

In a first embodiment, the invention comprises an implant for surgical use in humans or vertebrates for the replacement, for the partial replacement or for the strengthening of a damaged intervertebral disk or for the replacement, for the partial replacement or for the strengthening of a joint, which comprises at least one wire and/or at least one fiber.

The wire and/or the fiber is or are present at least partially as a knitted fabric. It is to be understood here that at least one or more wires or fibers can be used per knitted fabric. A knitted fabric has, by itself, great elasticity, which has a favorable effect on the flexibility of the implants produced therefrom.

In a particularly advantageous embodiment, the wire or the fiber is part of a knitted fabric. A knitted fabric is understood as meaning running meshes in succession, each new loop from which a mesh is formed being drawn through the mesh beforehand. Thus a particularly porous and extensible material is formed. An implant constructed from a knitted wire fabric has, under bending and under pressure stresses, both a high elasticity and a high internal damping. This is based on the fact that a force acting is distributed over and on a large number of contacts of the individual wires and/or fibers. Owing to internal friction of the wires and/or fibers in the individual meshes, oscillations, such as are initiated from outside on the body system, intervertebral disk and/or joints by walking, running and especially by jumping, are thus effectively damped. The knitted wire article according to the invention is at the same time reliably greatly deformable in its lift and decreases under pressure down to a minimal thickness.

Since the implant should make possible unrestricted movement in the course of natural movement (bending, tilting and rotating movements or else alternatively translation movements) and moreover should have the property of cushioning shocks and absorbing the shock energy, it is advantageous if said wire and/or said fiber is elastic or flexurally elastic, of course biocompatible and additionally low-wearing and abrasion-resistant and cannot be undesirably degraded by the body even over a relatively long period of time.

The wire and/or the fiber is therefore distinguished in that it comprises as a constituent at least titanium. A further biocompatible material which is employable in the present invention is, inter alia, stainless steel or alternatively a stainless steel alloy. Further employable materials, which are all currently used in medical implant applications, are alloys which contain, inter alia, as constituents in various quantitative proportions, titanium, cobalt, chromium, aluminum, vanadium, niobium and/or zirconium or stable plastics.

As becomes clear in the course of the description, however, under certain circumstances the use of a material resorbable by the body, i.e. which can be degraded by the body over time, can also be useful. Materials which can be used are, in particular, resorbable organic materials, in this case, inter alia, catgut, catgut chromium or collagen or else alternatively resorbable synthetic materials, such as organically degradable polymers, in this case, inter alia, Vicryl, Polysorb, Dexon, Piralac, Serafit, Bondek, Maxon or Panacryl.

Moreover, one or more of the materials can be integrated into a wire and/or fiber. Said materials are to be understood by way of example and are in no case restricted to said choice.

In the choice of the wire and/or fiber thickness, it should be taken into consideration that the diameter of a wire and/or a fiber is linked to its lifetime. In order to avoid the danger of breakage, the diameter of a wire and/or a fiber should not be chosen to be too thin. The wire and/or the fiber here has or have a diameter of approximately 0.01 mm to 5 mm, preferably of approximately 0.05 mm to approximately 1 mm and particularly preferably of approximately 0.2 mm to approximately 0.3 mm.

In addition to the choice of the wire or fiber material, the properties of the knitted fabric, however, are also influenced by the size and compactness of the meshes, it being possible to increase the compactness of the meshes in a shaping process step. This has effects on the properties of the knitted fabric or of the implant, in particular on the elasticity and thus also resilience and the shock absorption of the implant.

The knitted fabric in this case has a mesh width of 0.01 mm to 50 mm, preferably of 0.5 mm to 20 mm and particularly preferably of 3 mm to 8 mm.

In addition to the material, the diameter and the mesh width, the manner of production of the meshes is also of importance for the functionality of the implant. As already mentioned, a drawn-loop knitted fabric is advantageously used. This can also be prepared using a number of wires and/or fibers, e.g. in double-filament form. In principle, the knitted fabric, however, can also be present as a crocheted or formed-loop knitted fabric.

In particular, however, it has emerged that a knitted and in particular a circularly drawn-loop knitted fabric is to be preferred. Especially, it has proven to be particularly advantageous in production if the mesh material is circularly knitted and the knitted fabric is present as a knitted tube.

Alternatively, the wire and/or the fiber can, however, also be present as a nonwoven scrim, braid and/or as a textile.

In a further embodiment, it is possible here to increase the compactness of the meshes, namely if the knitted fabric is present as a pressed knitted fabric. This is done in a shaping process step. This has effects on the properties and in particular improves the elasticity and thus the resilience and damping properties of the implant and thus the ability to absorb shocks.

It has proven advantageous here if the knitted fabric is present as a rolled up, wound and/or folded knitted fabric and then pressed. As a result of the pressing, the wire and/or the fiber of the knitted fabric interlock with and/or become stuck to one another and in one another, by means of which these are connected to one another.

The knitted fabric is present after the pressing process as a pressed shaped article and has the form of a desired shaped article. As a result of the knitted fabric, cavities are formed here within the pressed shaped article.

These novel implants each show, after compression of the knitted fabric by the pressing process, a more or less great compressibility, which imparts a certain intrinsic resilience and internal damping to the implants.

The size of the cavities determined by the pressing process determines the properties of said shaped article with respect to rigidity, elasticity or flexural elasticity, compressibility, resilience and damping.

At the same time, the elasticity and damping and all other parameters (e.g. dimensions) are chosen according to the natural implants to be replaced.

The shaped article formed has the ability to adjust itself to the stresses due to elastic or plastic deformations without lasting damage owing to its flexibility and is insensitive to tilting and bending and imparts to the human or the vertebrate the ability to carry out bending, tilting and rotation movements or else alternatively translation movements.

In a particularly preferred embodiment of the invention, the shaped article has a spring constant which increases with elastic deformation. This guarantees an optimal resilience and damping of the shaped article or of the implant. Thus the implant is initially softly resilient and becomes harder with increasing deformation. This is particularly suitable for intervertebral disk prostheses.

The implant has a spring constant here which is between 5 and 3000 N/mm. In particular, initial spring constants, that is in the unloaded state, of between 5 and 300 N/mm, preferably between 15 and 200 N/mm, particularly preferably between 30 and 130 N/mm, are provided. With increasing deformation, the spring constant increases. In particular, the spring constant increases with increasing deformation approximately linearly to quadratically, so that an approximately quadratic or cubic force-path course results. Here, the implant can demonstrate a modified force-path course after incorporation into the body due to the adjacent tissue or the adjacent bone.

Since the shaped article is formed by the compressed knitted fabric and thus, in addition to the cavities, has a rough surface, and thus has porous properties, this makes possible an ingrowth of tissue and thereby makes it possible to connect the surrounding bone more strongly with the implant. Moreover, the cavities allow the accommodation of the tissue or bone abrasion occurring on rubbing of the implant on the surrounding tissue or bone, so that this abraded material does not remain between the surfaces sliding on one another.

In the actual embodiments, the implants should substantially be anatomically shaped, i.e. the dimensions and the shape of the implant should correspond essentially to the dimensions and the shape of the intervertebral disk to be replaced and/or of the anatomical joint to be replaced. However, for reasons of functionality in the production and in the incorporation of the implant it can also be advantageous under certain circumstances to choose another shape.

In one embodiment, the shaped article has a kidney-shaped design with a curved convex side and an opposite concave side and essentially corresponds here to the shape of a natural intervertebral disk.

In a further embodiment, the shaped article formed essentially corresponds to the shape of a natural hip joint socket or of a natural head of a femur.

In a further embodiment, the shaped article formed essentially corresponds to the shape of a natural shoulder joint socket or of a natural shoulder joint head.

The embodiments mentioned are to be understood by way of example and are in no case restricted to said selection. Without describing further joints in detail, the implant according to the invention can also be employed surgically in humans or vertebrates for the replacement, for the partial replacement or for the strengthening of other joints, for example knee joints, ankle joints, elbow joints, finger joints or toe joints.

As already described, under certain circumstances the use of a material resorbable by the body can be useful. This is provided in the particularly advantageous embodiment in which the implant is colonized with stem cells or with endogenous cells which are cultured in the laboratory. The great advantage here is that the new implant connects strongly with the bone, while, for example, implants of plastic or other materials loosen with time and/or can lead to foreign body reactions. Here, the knitted fabric forming the implant serves as a support structure. The knitted fabric can comprise one or more of said resorbable materials and/or one or more of said biocompatible materials, in particular titanium, which then remains permanently in the body as a support structure.

The wire diameter and/or the mesh width is or are chosen here in order to make possible a simple ingrowth of the stem cells or of the endogenous cells.

If, for example, catgut colonized with stem cells is used, it is even conceivable for the implant to transform at least partially into natural tissue.

In addition, the present invention comprises a process for the production of an implant for surgical use in humans or vertebrates, in particular for the production of an implant according to the foregoing description, for the replacement, for the partial replacement or for the strengthening of a damaged intervertebral disk or for the replacement, for the partial replacement or for the strengthening of an anatomical joint, which comprises making available at least one wire and/or at least one fiber.

Here, at least one wire and/or at least one fiber is or are made available which contains or contain at least titanium as a constituent.

As an alternative thereto, at least one wire and/or at least one fiber can be made available which contains or contain as a constituent at least one biocompatible material, in particular stainless steel or a stainless steel alloy. Further materials which can be employed, which are all presently used in medical implant applications, are alloys which, inter alia, contain as constituents in various quantitative proportions titanium, cobalt, chromium, aluminum, vanadium, niobium and/or zirconium or stable plastics.

A further possibility consists in making available at least one wire and/or at least one fiber which contains or contain as a constituent at least one material resorbable by the body. Materials which can be used are in particular resorbable organic materials, in this case in particular catgut, catgut chromium or collagen or else alternatively resorbable synthetic materials, such as organically degradable polymers, in this case, inter alia, Vicryl, Polysorb, Dexon, Piralac, Serafit, Bondek, Maxon or Panacryl. The wire and/or the fiber is or are made available with a diameter of approximately 0.01 mm to 5 mm, preferably of approximately 0.05 mm to approximately 1 mm and particularly preferably of approximately 0.2 mm to approximately 0.3 mm.

It has proven here to be particularly advantageous if the wire and/or the fibers is or are made available at least partially as a knitted fabric. In this case, one or more wires/fibers per knitted fabric can also be processed.

The knitted fabric is in this case made available with a mesh width of 0.01 mm to 5 mm, preferably from 0.1 mm to 1 mm and particularly preferably from 0.2 mm to 0.5 mm.

It has emerged as particularly advantageous if the knitted fabric is made available as a drawn-loop knitted fabric. Further possibilities for the production of knitted fabrics comprise crocheting or formed-loop knitting.

Further possibilities consist in making available the wire and/or of the fiber as a nonwoven scrim, braid or as a textile.

In the production of the knitted fabric, production by means of circular knitting has proven particularly advantageous, since the knitted fabric is thereby made available as a tube and thus has no sharp edges and can be knitted or circularly knitted without seams. A piece of such an endless tube of the necessary length is then cut off.

The dimensions of the tube, i.e. its diameter and its length, depend on the dimensions and the properties, especially with respect to rigidity, elasticity, resilience and damping, of the shaped article to be formed and are determined empirically in a series of tests.

For reasons of improved elasticity, it has proven extremely advantageous not to use the knitted fabric immediately after knitting, but subsequently to additionally subject it to a shaping treatment. In this shaping treatment, the knitted fabric is preferably compressed, by means of which the wire and/or the fiber lay closer to one another.

In a next process step, the knitted fabric or the tube formed by the knitted fabric is converted into the form of a band by pressing and/or rolling.

The band is pressed and/or rolled here in such a way that the band preferably has a thickness of approximately 0.1 mm to approximately 20 mm and particularly preferably of approximately 0.75 mm to approximately 2 mm. The mesh width of the band, however, still corresponds here to the mesh width of the tube.

In a further process step, the band formed by the knitted fabric is converted into a wavy or corrugated form by deformation. After this process step, the band is thus essentially present in the form of a wave.

The band is converted here into a wavy form in such a way that the wave axes run parallel to one another. The distance between two adjacent wave crests has a value of 0.01 mm to 100 mm, preferably a value of approximately 0.1 mm to 5 mm and particularly preferably a value of approximately 1 mm to approximately 3 mm. The height difference between wave trough and wave crest has a value of approximately 0.01 mm to approximately 100 mm and preferably a value of approximately 0.5 mm to approximately 10 mm and particularly preferably of 1 mm to 5 mm.

The wavy or corrugated shape of the band is chosen here in such a way that the wave axis, i.e. the axis perpendicular to the direction of propagation of the wave, includes, with the longitudinal axis of the band, an angle á of approximately 0° to approximately 90°, preferably of approximately 10° to approximately 60° and particularly preferably of approximately 25° to approximately 35°.

In a next process step, the knitted fabric per se or the knitted fabric present as a corrugated or uncorrugated band is rolled up, wound and/or folded.

The rolled up, wound or folded article is subjected in a next process step to a shaping process.

By means of a pressing process, the rolled up, wound or folded article is converted into the form of a desired shaped article.

In this shaping process by means of pressing, the rolled up, wound or folded article formed by the band or the knitted fabric is reduced in its volume by a factor of approximately 1/20 to 9/10, preferably of approximately 1/10 to 1/2 and particularly preferably of approximately 1/5 to 1/3. Since the shaped article is elastic and expands again after the pressing process, the shaped article is compressed significantly more strongly in its dimensions during the compression. The compression performed on a certain volume moreover determines the number of permissible stresses and thus the lifetime of the implant according to the invention.

The wires and/or fibers of the knitted fabric intermesh with and become stuck to one another and in one another as a result of the pressing process and join together by means of this.

In this process step, cavities are formed by the knitted fabric within the pressed shaped article, which, since the starting material was a knitted article, are distributed randomly but uniformly in the shaped article. The cavities formed within the pressed shaped article have a diameter of approximately 0.001 mm to approximately 10 mm, preferably of approximately 0.04 mm to approximately 2.0 mm and particularly preferably of approximately 0.2 mm to approximately 1.0 mm.

As a result of the production process of the implant, influence can specifically be exerted on its rigidity, elasticity, resilience and damping properties. The properties are determined by the specific choice of the material, the wire or fiber diameter, the mesh width, the height and the width of the waves, and their angle á to the longitudinal direction of the band and the strength of the compression in the pressing process, since as a result of the pressing pressure chosen the compression of the knitted fabric is specifically influenced and thus the size of the cavities remaining between the wires and/or the fibers is determined. The individual parameters are determined empirically here in a series of experiments. Thus the properties of the shaped article to be formed or of the implant to be formed on the properties of the intervertebral disk to be replaced or of the joint to be replaced can be optimally adjusted so that the implant optimally handles the local stress in its function and makes possible an improved transfer of force from the implant to the bone.

The shaped article formed by the pressing process can in this case essentially have the desired shape of a human intervertebral disk. The shaped article formed is of kidney-shaped design with a curved convex side and an opposite concave side.

For example, an intervertebral disk manufactured by this process can be anchored with the adjacent vertebrae using processes known in the field of joint replacement, for example by means of a press fit or by a cementation process.

Since the shaped article is formed by the compressed knitted fabric and thus has a rough surface in addition to the cavities, this makes possible an ingrowth of tissue and makes it possible to connect the surrounding bone more strongly with the implant. This necessitates no further means, such as, for example, in the prior art mentioned in the description. There, the implants have projections which position the vertebrae against the disk and retain them in position.

Compared with conventional implants, which in general are of multicomponent design and can be implanted into the body via their components, the present implant can be implanted as a one-piece unit and thus excessive stress on the surrounding anatomical structures and thus the patient can be avoided.

The intervertebral disk according to the invention can be used directly as an implant for surgical use in humans or vertebrates for the replacement of a damaged intervertebral disk. The invention, however, also relates to the use of the implant according to the invention as part of an intervertebral disk implant, which comprises an upper plate, a lower plate and, as an elastic core, said implant, which is arranged between the plates and adjoins them.

The intervertebral disk according to the invention can therefore be employed in DE 694 28 143 T2 as a replacement for the elastomeric core mentioned in the description and grants the intervertebral disk described there a longer life.

Furthermore, the compressed knitted fabric can also be used as a ball joint bearing system in the mentioned DE 696 23 535 T2 and imparts to the artificial intervertebral disk implant the ability to absorb shocks to the vertebral column.

In a further embodiment, the shaped article can moreover be designed in such a way that it essentially corresponds to the shape of a natural hip joint socket or of a natural head of a femur. Furthermore, the shaped article can be designed in such a way that it essentially corresponds to the shape of a natural shoulder joint socket or of a natural shoulder joint head. Without describing further joints in detail, the shaped article according to the invention can also be designed in such a way that it can be surgically implanted for the replacement, for the partial replacement or for the strengthening of other joints in the human body or in vertebrates, for example knee joints, ankle joints, elbow joints, finger joints or toe joints.

The joint according to the invention can thus be used directly as an implant for surgical use in humans or vertebrates for the replacement of a joint. The invention, however, also relates to the use of the implant according to the invention as part of a joint implant, comprising a joint socket and/or a joint head, which in each case are formed by at least plastics, metal or ceramics and said implant is arranged on the side facing away from the joint surfaces rubbing on one another, i.e. in the direction of the bone, and adjoins this. The known material combinations for the formation of a joint coupling, i.e. for the formation of joint socket and joint head or for the formation of the joint socket and joint head surfaces rubbing on one another, such as, for example, plastic/plastic, metal/metal, plastic/metal, plastic/ceramic or ceramic/ceramic, are only moderately adjustable in their properties with respect to rigidity, elasticity, resilience and damping in order to deal with the functions of the joint to be replaced.

As a result of the production process of the implant according to the invention, however, influence can be specifically exerted on its stiffness, elasticity, resilience and damping properties, so that it can be optimally adjusted to the functions of the joint to be replaced. Thus, joint pairings proven with respect to low wear due to decreased abrasion can exhibit improved elasticity adjusted to the bone elasticity by combination with the implant according to the invention and thus guarantee an optimized transfer of force from the implant to the bone. The transfer of force from the implant to the bone here plays a crucial role in the question of the long-term anchoring of the implant in the body. Moreover, since the shaped article is formed by the compressed knitted fabric and thus has a rough surface in addition to the cavities, this additionally makes possible an ingrowth of the surrounding bone, as a result of which this connects more strongly with the implant, which means an improvement in the long-term anchoring of the implant in the body.

In one particular embodiment, in a further process step the implant formed from a knitted fabric can be colonized with stem cells in which the knitted fabric takes over the function of a structure.

Moreover, the present invention comprises an implant for surgical use in humans or vertebrates for the replacement, for the partial replacement or for the strengthening of a damaged intervertebral disk or for the replacement, for the partial replacement or for the strengthening of a joint, which can be produced using the above process.

The invention moreover relates to the use of knitted fabrics for the production of implants for surgical use in humans or vertebrates for the replacement, for the partial replacement or for the strengthening of a damaged intervertebral disk or for the replacement, for the partial replacement or for the strengthening of a joint.

The invention further comprises an implant which comprises a wire resorbable by the body and/or a resorbable fiber and the wire or the fiber is colonized at least sectionwise with stem cells.

This implant according to the invention is suitable as a replacement material for a great variety of applications. For example, in the case of bone fractures whose healing proves difficult, knitted articles colonized with stem cells could be used, with whose aid the bone could be surrounded and stabilized. As a result of the stem cells, for example, new bone material can be formed.

It is conceivable to replace a great variety of parts of a body with a knitted article colonized with stem cells.

The invention will be illustrated below with the aid of an exemplary embodiment.

DETAILED DESCRIPTION OF THE INVENTION

Figure 1:
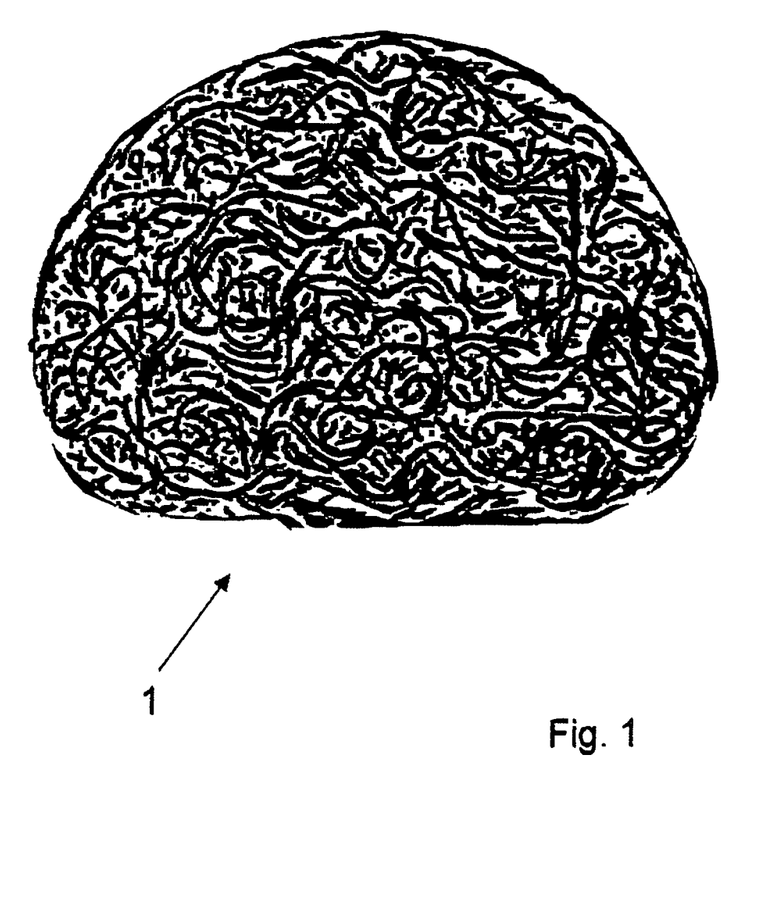
FIG. 1 shows a schematic representation of an intervertebral disk prosthesis according to the invention.

FIG. 1 shows an intervertebral disk prosthesis 1 in plan view. The intervertebral disk prosthesis 1 has approximately the cross section of a natural intervertebral disk. The intervertebral disk prosthesis 1 according to the exemplary embodiment consists of titanium wire having a diameter of 0.23 mm, is approximately 5 mm high and weighs about 4 g. The titanium wire was first knitted as a knitted fabric. The knitted article (FIGS. 2 and 3) was pressed in the shape of the intervertebral disk prosthesis 1. The intervertebral disk prosthesis 1 thus resulting is biocompatible and fits the vertebral bodies due to its elastic structure. The surface of the intervertebral disk prosthesis 1 enters into a partly positive connection with the biological tissue so that the intervertebral disk prosthesis 1 is secured against slipping out without further means.

Figure 2:
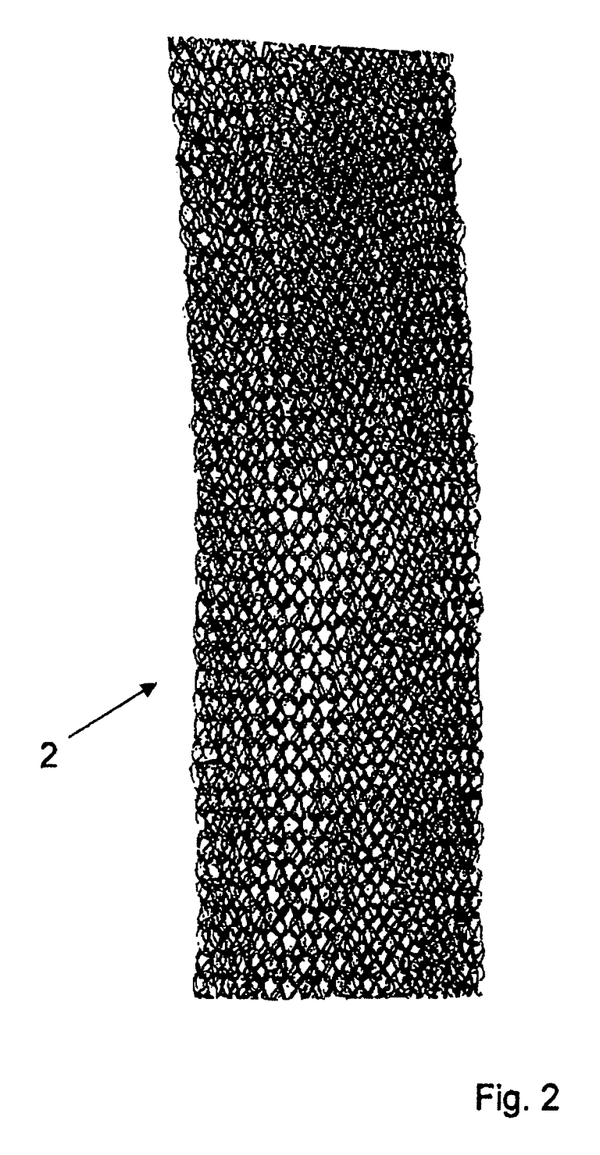
FIG. 2 shows the schematic representation of a knitted article, from which the intervertebral disk prosthesis according to FIG. 1 is formed.

FIG. 2 shows the starting material for an implant according to the invention. This is a knitted article 2 of titanium wire, which has the shape of a tube. The knitted article is pressed in the shape of an implant.

Figure 3:
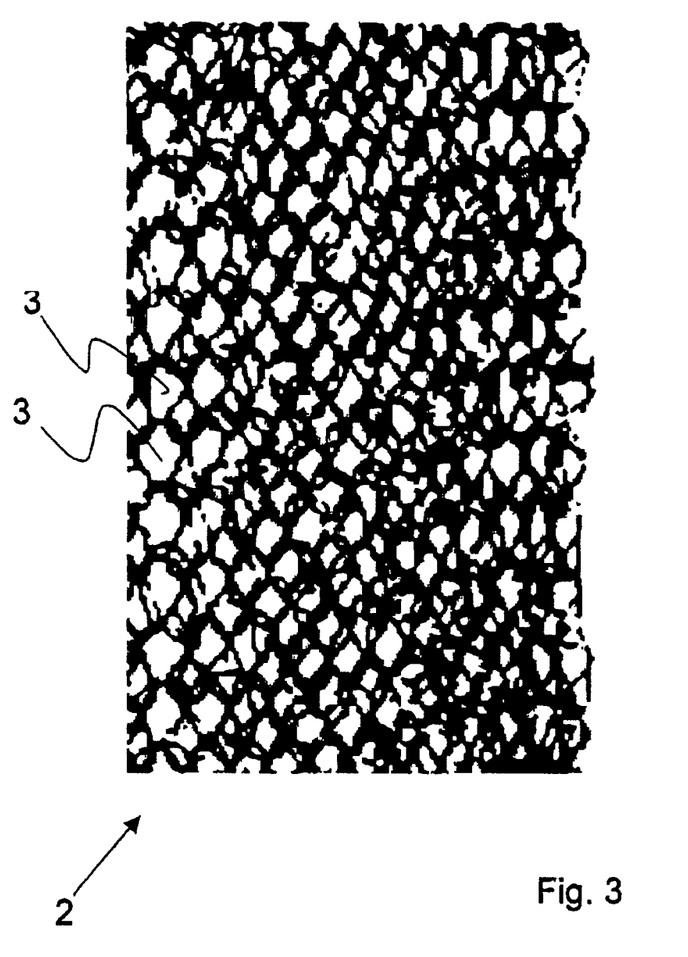
FIG. 3 shows a close-up view of FIG. 2.

FIG. 3 shows a close-up view of FIG. 2. It can readily be seen how the individual meshes 3 engage in one another.

Figure 4:
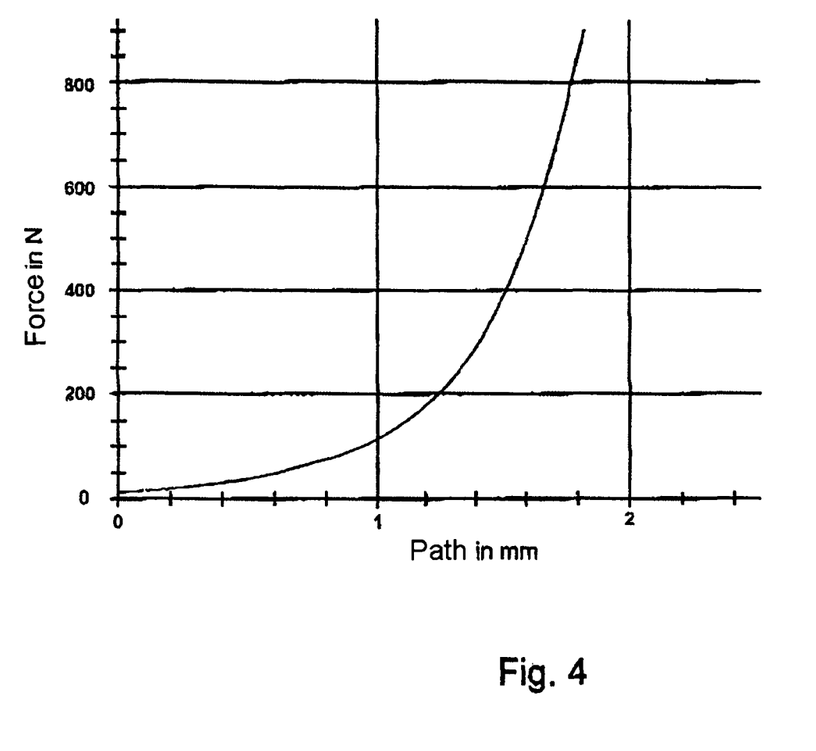
FIG. 4 shows an exemplary force-path curve of an intervertebral disk prosthesis according to the invention.

FIG. 4 shows an exemplary force-path course of an intervertebral disk prosthesis according to the invention. On the x axis, the deformation of the intervertebral disk is plotted in mm, and on the y axis the force in N. It can be seen that no linear force-path course exists, but that the force increases approximately quadratically to cubically. The prosthesis is thus initially softly resilient and then becomes harder. The resilience constant F of the intervertebral disk prosthesis increases here approximately linearly to quadratically.

Figure 5:
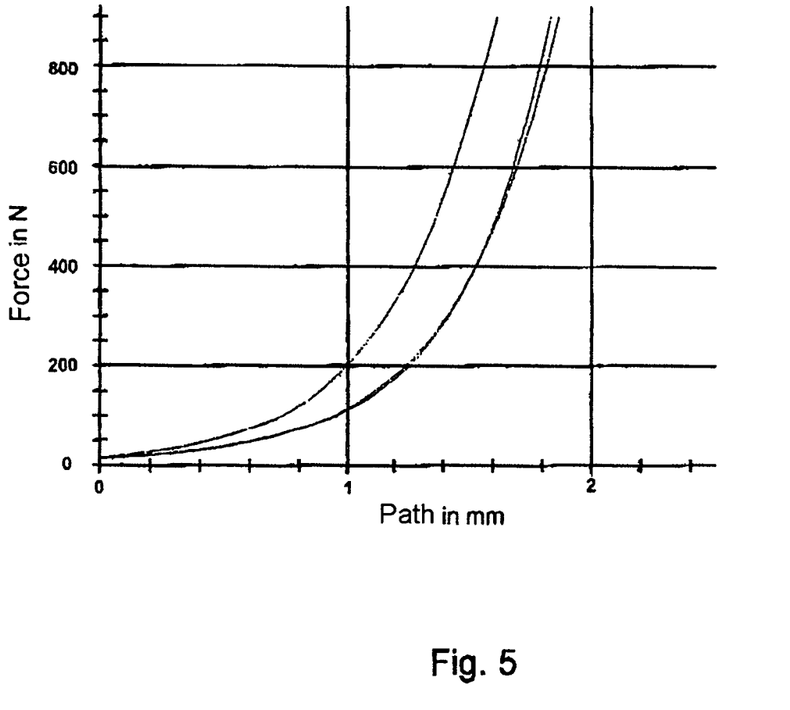
FIG. 5 likewise shows exemplary force-path curves of intervertebral disk prostheses according to the invention.

FIG. 5 shows further curves of an exemplary force-path course of various exemplary embodiments of an intervertebral disk prosthesis. The characteristics of the prosthesis can be varied.

The invention claimed is:

1. An implant for surgical use in humans or vertebrates for replacement, for partial replacement or for strengthening of a damaged inter-vertebral disk, wherein the implant is elastic and has resilient and damping properties, the implant comprising:
    at least one wire, wherein the at least one wire comprises at least partially a knitted fabric, the knitted fabric being selected from the group consisting of a rolled up knitted fabric, a wound knitted fabric, a folded knitted fabric, and combinations thereof, the knitted fabric having a pressed shape with a kidney-shaped design including a curved convex side and an opposite concave side so that the pressed shape corresponds to a shape of a natural inter-vertebral disk,
    wherein the at least one wire comprises at least one biocompatible material selected from the group consisting of titanium, stainless steel, stainless steel alloys, and titanium alloys, and
    wherein the implant has a resilience constant that increases with increasing elastic deformation between 5 and 3000 N/mm and is initially between 5 and 300 N/mm.

2. The implant as claimed in claim 1, wherein the at least one wire comprises at least one material resorbable by the body.

3. The implant as claimed in claim 1, wherein the at least one wire has a diameter of 0.01 mm to 5 mm.

4. The implant as claimed in claim 1, wherein the knitted fabric has a mesh width of 0.01 mm to 50 mm.

5. The implant as claimed in claim 4, wherein the knitted fabric is a drawn-loop knitted fabric.

6. The implant as claimed in claim 4, wherein the knitted fabric is a crocheted knitted fabric.

7. The implant as claimed in claim 4, wherein the knitted fabric is a formed-loop knitted fabric.

8. The implant as claimed in claim 1, wherein the at least one wire is at least partially in a nonwoven scrim.

9. The implant as claimed in claim 1, wherein the at least one wire is at least partially in a braid.

10. The implant as claimed in claim 1, wherein the at least one wire is at least partially in a textile.

11. The implant as claimed in claim 1, wherein the knitted fabric is a tube.

12. The implant as claimed in claim 1, wherein the at least one wire is interlocked with the knitted fabric.

13. The implant as claimed in claim 1, wherein the at least one wire is stuck to the knitted fabric.

14. The implant as claimed in claim 1, wherein the at least one wire is in the knitted fabric.

15. The implant as claimed in claim 1, further comprising cavities formed in the pressed shape, wherein the cavities each have a diameter of 0.001 mm to 10 mm.

16. The implant as claimed in claim 1, wherein the resilience constant increases linearly with increasing elastic deformation.

17. The implant as claimed in claim 1, wherein the resilience constant increases quadratically with increasing elastic deformation.

* * * * *